US011052006B2

(12) United States Patent
Tanaka

(10) Patent No.: US 11,052,006 B2
(45) Date of Patent: Jul. 6, 2021

(54) ASPIRATOR OR PRESSURIZER

(71) Applicant: Murata Manufacturing Co., Ltd., Kyoto (JP)

(72) Inventor: Nobuhira Tanaka, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 913 days.

(21) Appl. No.: 15/401,552

(22) Filed: Jan. 9, 2017

(65) Prior Publication Data

US 2017/0112697 A1 Apr. 27, 2017

Related U.S. Application Data

(63) Continuation of application No. PCT/JP2015/069851, filed on Jul. 10, 2015.

(30) Foreign Application Priority Data

Jul. 11, 2014 (JP) .............................. JP2014-143125

(51) Int. Cl.
*A61G 7/057* (2006.01)
*A61M 1/00* (2006.01)

(52) U.S. Cl.
CPC ............... *A61G 7/057* (2013.01); *A61M 1/00* (2013.01); *A61M 1/008* (2013.01); *A61M 1/0066* (2013.01); *A61M 2205/3334* (2013.01); *A61M 2205/583* (2013.01); *A61M 2210/0618* (2013.01)

(58) Field of Classification Search
CPC .... F04B 43/046; F04B 43/095; F04B 17/003; A61M 1/00; A61M 1/0066; A61M 1/008; A61M 2205/3334; A61M 2205/583; A61M 2210/0618; A61M 1/0031; (Continued)

(56) References Cited

U.S. PATENT DOCUMENTS 4,825,904 A * 5/1989 Grau ................... F16K 31/0682
137/554
6,106,494 A * 8/2000 Saravia ............... A61M 3/0258
604/151

(Continued)

FOREIGN PATENT DOCUMENTS

JP 2000060962 A 2/2000
JP 2001218831 A 8/2001
(Continued)

OTHER PUBLICATIONS

Extended European Search Report for 15 81 8979 dated Feb. 5, 2018.
(Continued)

*Primary Examiner* — Connor J Tremarche
(74) *Attorney, Agent, or Firm* — Pearne & Gordon LLP

(57) ABSTRACT

An aspirator includes a pump, a detecting unit, and a control unit. The pump is driven by a piezoelectric element and has a suction portion and a discharge portion. The detecting unit includes a current detector and a regulator, and detects a closed state of the suction portion. The control unit includes the regulator and a voltage controller, and regulates an output voltage for the piezoelectric element in accordance with the closed state of the suction portion detected by the detecting unit.

9 Claims, 13 Drawing Sheets

(58) Field of Classification Search
CPC .... A61M 2205/3337; A61M 2017/246; A61M 2205/14
USPC .......................................................... 417/19
See application file for complete search history.

(56) References Cited

U.S. PATENT DOCUMENTS

| | | | |
|---|---|---|---|
| 6,471,679 B1 | 10/2002 | Suh | |
| 2003/0111933 A1* | 6/2003 | Gallmeyer | H01L 41/042 310/317 |
| 2006/0147329 A1* | 7/2006 | Tanner | F04B 7/00 417/505 |
| 2008/0154183 A1* | 6/2008 | Baker | A61M 1/0058 604/28 |
| 2009/0118663 A1 | 5/2009 | Rockley | |
| 2009/0243431 A1 | 10/2009 | Ohsawa | |
| 2010/0076366 A1* | 3/2010 | Henderson, Sr. | A61B 5/031 604/9 |
| 2010/0195851 A1* | 8/2010 | Buccafusca | H04R 17/02 381/190 |
| 2011/0190670 A1 | 8/2011 | Jaeb et al. | |
| 2011/0251569 A1 | 10/2011 | Turner et al. | |
| 2012/0282111 A1* | 11/2012 | Nip | F04B 49/06 417/48 |
| 2013/0052044 A1 | 2/2013 | Matsuzaki et al. | |
| 2014/0107579 A1* | 4/2014 | Lanigan | A61M 39/12 604/151 |
| 2014/0116519 A1* | 5/2014 | Brown | F16K 37/0058 137/1 |

FOREIGN PATENT DOCUMENTS

| | | |
|---|---|---|
| JP | 2007117273 A | 5/2007 |
| JP | 2010527636 A | 8/2010 |
| JP | 2013050034 A | 3/2013 |
| JP | 2013532246 A | 8/2013 |

OTHER PUBLICATIONS

Written Opinion of WO2016/006677 dated Sep. 1, 2015.
International search report of WO2016/006677 dated Sep. 1, 2015.

* cited by examiner

FIG. 3
FIG. 3A
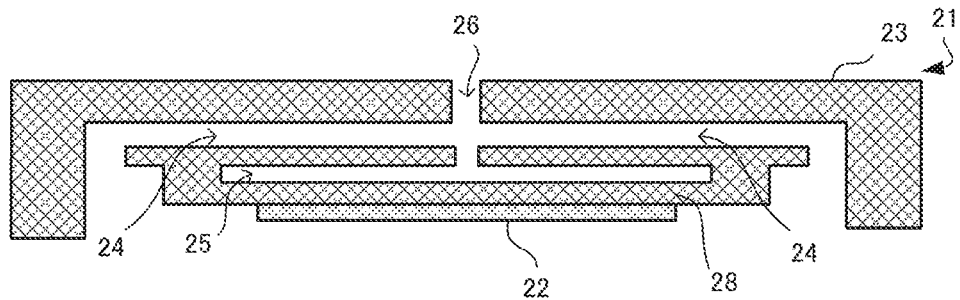
FIG. 3B
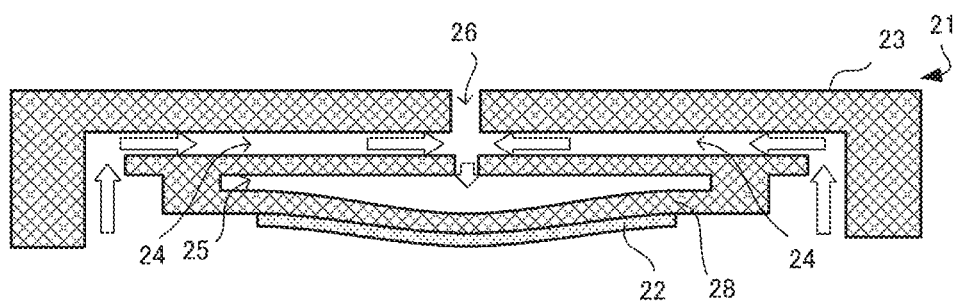
FIG. 3C
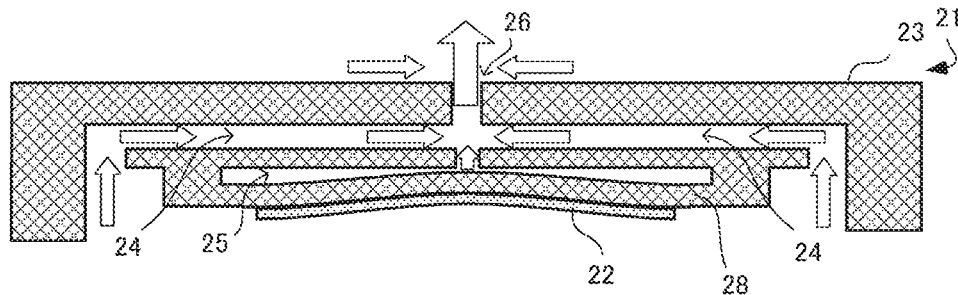
FIG. 4
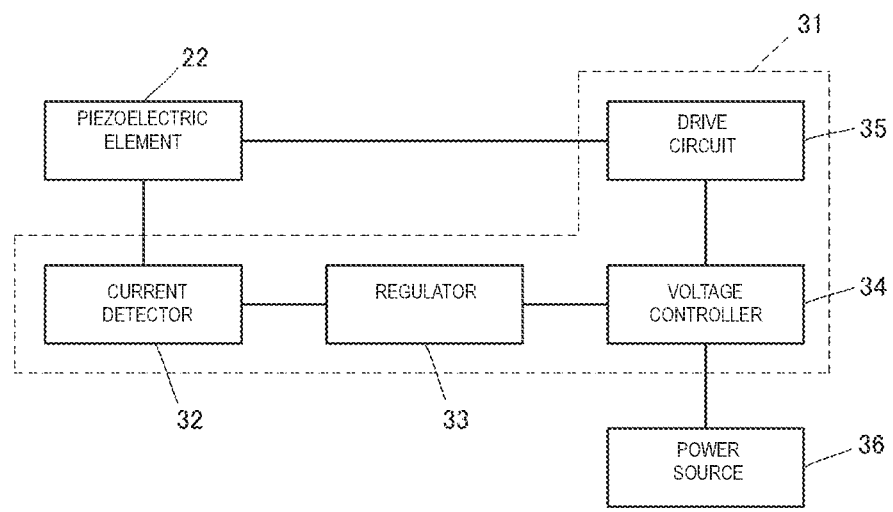

ASPIRATOR OR PRESSURIZER

This application is a continuation of International Application no. PCT/JP2015/069851 filed on Jul. 10, 2015 which claims priority from Japanese patent application no. JP 2014-143125 filed on Jul. 11, 2014. The contents of these applications are incorporated herein by reference in their entireties.

BACKGROUND

Technical Field

The present disclosure relates to an aspirator or pressurizer including a pump.

Examples of conventional aspirators include a nasal mucus aspirator described in Patent Document 1. The nasal mucus aspirator includes a vacuum generator, a nasal mucus storage cylinder, a suction tube, and an actuator. The vacuum generator and the nasal mucus storage cylinder are coupled to each other by a tube. The nasal mucus storage cylinder is coupled to the suction tube for suctioning nasal mucus. The actuator is configured to start and stop suctioning of the nasal mucus. In this nasal mucus aspirator, when the suction tube is inserted into a nasal cavity and a button of the actuator is pressed, the nasal mucus is suctioned from the suction tube by a vacuum generated by the vacuum generator, and then is stored in the nasal mucus storage cylinder. When the button of the actuator is released, the vacuum is released and the suctioning is stopped.

Examples of conventional pressurizers include one that is used in an anti-bedsore bed. In a conventional anti-bedsore bed, air cells inflated by being pressurized by a pressurizer raise one side of the user's body. This allows the user to turn over, thereby preventing a user's bedsore.

Patent Document 1: Japanese Unexamined Patent Application Publication No. 2001-218831

BRIEF SUMMARY

In the nasal mucus aspirator described in Patent Document 1, since suctioning continues at constant suction pressure, the suction pressure of the nasal mucus aspirator needs to be set high to ensure reliable suctioning of the nasal mucus. However, this increases the power consumption of the nasal mucus aspirator during operation. Additionally, if the suction tube does not successfully hit the nasal mucus, a large amount of air may be suctioned all at once from the nasal cavity, and this may negatively affect the human body. On the other hand, if the suction pressure of the nasal mucus aspirator is set low to avoid the problems described above, nasal mucus of high viscosity may not be able to be removed. Since the conventional anti-bedsore bed is unable to detect the turning of the user, the pressurizer applies excessive pressure to the air cells for a long period of time. This results in increased power consumption and noise of the pressurizer.

The present disclosure provides an aspirator or pressurizer capable of applying appropriate pressure in accordance with the situation.

An aspirator or pressurizer according to the present disclosure includes a pump, a detecting unit, and a control unit. The pump is driven by a piezoelectric element and has a suction portion and a discharge portion. The detecting unit is configured to detect a closed state of the suction portion or the discharge portion. The control unit is configured to regulate an output voltage for the piezoelectric element in accordance with the closed state of the suction portion or the discharge portion detected by the detecting unit.

With this configuration, the output voltage for the piezoelectric element is automatically regulated in accordance with the closed state of the suction portion. For example, when it is difficult to suction nasal mucus, the amplitude of the output voltage is increased and the nasal mucus is suctioned by high suction pressure. When it is easy to suction nasal mucus, the amplitude of the output voltage is set to a medium level and the nasal mucus is suctioned by low suction pressure. When suctioning of nasal mucus is completed or there is no nasal mucus, the amplitude of the output voltage is reduced. Since the aspirator can thus be operated by a minimum voltage, its power consumption during operation can be reduced.

The amplitude of the output voltage is increased only when it is difficult to suction the nasal mucus. In other words, the amplitude of the output voltage is reduced when suctioning of the nasal mucus is completed or there is no nasal mucus. Thus, since it is unlikely that a large amount of air is suctioned out of the nasal cavity, a negative impact on the human body can be reduced.

When the pressurizer is used in an anti-bedsore bed, the closed state of the discharge portion of the pump varies depending on whether the user has turned over. Therefore, with the configuration of the present disclosure, the output voltage for the piezoelectric element is automatically regulated depending on whether the user has turned over. Thus, by simply driving the pump for a minimum period of time at a minimum output, it is possible to allow the user to turn over and prevent a user's bedsore. That is, the power consumption and noise of the pressurizer used in the anti-bedsore bed can be reduced.

In the aspirator or pressurizer according to the present disclosure, the detecting unit may detect a pressure difference between the suction portion and the discharge portion. The pressure difference between the suction portion and the discharge portion varies depending on whether the suction portion or the discharge portion is closed. Therefore, with this configuration, the closed state of the suction portion or the discharge portion can be detected by detecting the pressure difference between the suction portion and the discharge portion. Also, by varying the amplitude of the output voltage in a stepwise manner and detecting the suction pressure accordingly, the level of difficulty in suctioning the nasal mucus can be determined.

In the aspirator or pressurizer according to the present disclosure, the detecting unit may detect a rate of flow from the suction portion to the discharge portion. The rate of flow varies depending on whether the suction portion or the discharge portion is closed. Therefore, with this configuration, in the same manner as above, the closed state of the suction portion or the discharge portion can be detected by detecting the rate of flow.

In the aspirator or pressurizer according to the present disclosure, the detection by the detecting unit can involve using an impedance of the piezoelectric element. An amount related to the impedance of the piezoelectric element, such as the magnitude or phase of the impedance of the piezoelectric element or a frequency at which the magnitude of the impedance of the piezoelectric element is minimized, varies depending on whether the suction portion or the discharge portion is closed. Therefore, with this configuration, the closed state of the suction portion or the discharge portion can be detected by using the impedance of the piezoelectric element.

In the aspirator or pressurizer according to the present disclosure, the detection by the detecting unit may involve using a magnitude of the impedance of the piezoelectric element at a drive frequency of the pump. The magnitude of the impedance of the piezoelectric element is the amplitude ratio between the current flowing through the piezoelectric element and the output voltage for the piezoelectric element. Therefore, with this configuration, the closed state of the suction portion or the discharge portion can be detected by measuring the current flowing through the piezoelectric element. Also, in the case of measuring the current, the number of components of a circuit implementing the detecting unit can be reduced. It is thus possible to reduce the size of the circuit implementing the detecting unit.

In the aspirator or pressurizer according to the present disclosure, the detection by the detecting unit may involve using a phase of the impedance of the piezoelectric element at a drive frequency of the pump. The phase of the impedance of the piezoelectric element is a phase difference between the current flowing through the piezoelectric element and the output voltage for the piezoelectric element. Therefore, with this configuration, the closed state of the suction portion or the discharge portion can be detected by measuring the phase difference between the current flowing through the piezoelectric element and the output voltage for the piezoelectric element. Also, since the measurement of the phase difference is less affected by changes in temperature, it is possible to accurately regulate the suction pressure or pressurizing force.

In the aspirator or pressurizer according to the present disclosure, the detection by the detecting unit may involve using a frequency at which a magnitude of the impedance of the piezoelectric element is minimized. The frequency at which the magnitude of the impedance of the piezoelectric element is minimized is a resonant frequency of the piezoelectric element. Therefore, with this configuration, the closed state of the suction portion or the discharge portion can be detected by calculating the resonant frequency of the piezoelectric element. Also, by adjusting the drive frequency of the pump to the resonant frequency, it is possible to increase the vibration of the piezoelectric element and achieve high suction pressure or pressurizing force without necessarily varying the amplitude of the output voltage.

The aspirator or pressurizer according to the present disclosure may further include an indicator configured to display the closed state of the suction portion or the discharge portion detected by the detecting unit. With this configuration, the closed state of the suction portion or the discharge portion can be displayed by the indicator.

In the aspirator according to the present disclosure, an object to be suctioned may be nasal mucus. With this configuration, nasal mucus can be suctioned.

According to the present disclosure, an aspirator or pressurizer capable of applying appropriate pressure in accordance with the situation can be obtained.

BRIEF DESCRIPTION OF DRAWINGS

FIGS. 3A-3C are schematic diagrams illustrating different vibration modes of the piezoelectric pump according to the first embodiment.

FIG. 4 is a block diagram of a circuit unit according to the first embodiment.

DETAILED DESCRIPTION

First Embodiment

Figure 1:
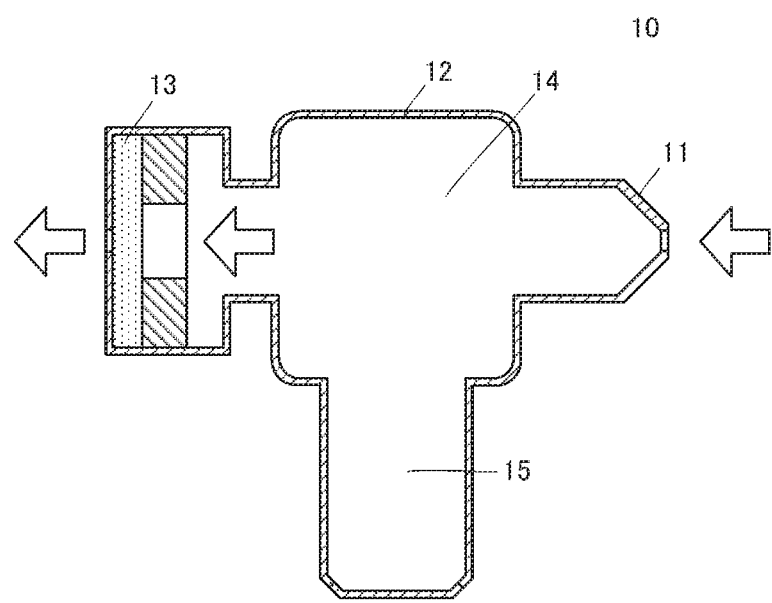
FIG. 1 is a schematic cross-sectional view of an aspirator according to a first embodiment.

An aspirator 10 according to a first embodiment of the present disclosure will be described. The aspirator 10 is used to suction nasal mucus. FIG. 1 is a schematic cross-sectional view of the aspirator 10. The aspirator 10 includes a nozzle 11, a separator 12, and a piezoelectric drive unit 13 arranged in this order from front to rear. The aspirator 10 has a flow passage 14 that connects the front end of the nozzle 11 to the rear end of the piezoelectric drive unit 13. The separator 12 includes a storage unit 15 that branches off the flow passage 14. The piezoelectric drive unit 13 includes a piezoelectric pump 21 (see FIG. 2) and a circuit unit 31 (see FIG. 4) for driving the piezoelectric pump 21. The piezoelectric pump 21 corresponds to a pump of the present disclosure. The aspirator 10 includes an indicator (not shown) configured to display the state of the front end of the nozzle 11.

In the aspirator 10, the front end of the nozzle 11 is inserted into the nasal cavity for suctioning nasal mucus. When the piezoelectric drive unit 13 is driven, a flow of air from the front end of the nozzle 11 to the rear end of the piezoelectric drive unit 13 is generated in the flow passage 14. Nasal mucus in the nasal cavity is suctioned from the front end of the nozzle 11 together with air, separated in the separator 12, and stored in the storage unit 15.

Figure 2:
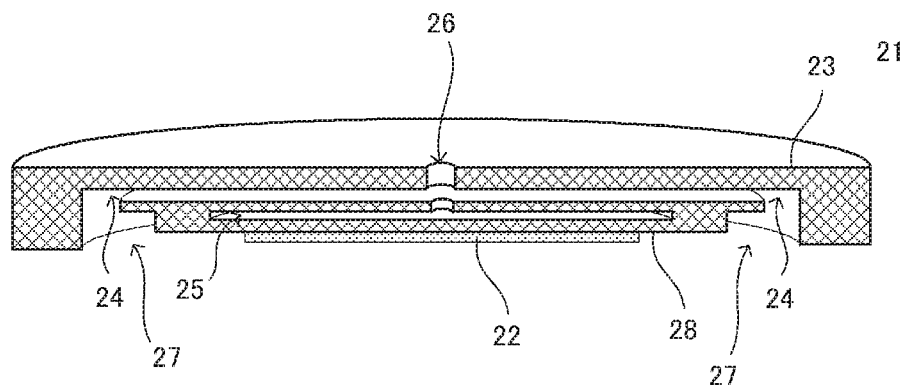
FIG. 2 is a cross-sectional view of a piezoelectric pump according to the first embodiment.
Figure 2:

FIG. 2 is a cross-sectional view of the piezoelectric pump 21. The piezoelectric pump 21 includes a piezoelectric element 22 and a structure 23. The structure 23 has a generally disk-like outer shape and is thin in the thickness direction. A discharge port 26 is open near the center of the top surface of the structure 23. A suction port 27 is open near the edge of the bottom surface of the structure 23. The piezoelectric pump 21 is positioned with the suction port 27 facing the nozzle 11. The discharge port 26 corresponds to a discharge portion of the present disclosure. The suction port 27 corresponds to a suction portion of the present disclosure.

The structure 23 is internally provided with a flow passage 24 and a pump chamber 25. The flow passage 24 communicates with the discharge port 26 on the top surface of the structure 23. In the structure 23, the flow passage 24 extends from around the center toward the outer edge of the structure 23, and communicates with the suction port 27 on the bottom surface of the structure 23. The pump chamber 25 is a thin circular cylindrical space provided on the bottom side of the portion where the discharge port 26 and the flow passage 24 communicate with each other. The pump chamber 25 is open to the portion where the discharge port 26 and the flow passage 24 communicate with each other.

The inner bottom surface of the pump chamber 25 in the structure 23 is configured as a diaphragm (vibrating plate) 28 capable of bending and vibrating. The diaphragm 28 has a disk-like shape. The top surface of the diaphragm 28 faces the pump chamber 25, and the piezoelectric element 22 is affixed to the bottom surface of the diaphragm 28. The top surface of the diaphragm 28 is disposed opposite the discharge port 26, with the pump chamber 25 interposed therebetween. The piezoelectric element 22 is a disk-shaped member which is thin in the thickness direction. The piezoelectric element 22 has piezoelectricity which allows the piezoelectric element 22 to expand and contract in the in-plane direction of the principal surface thereof by being subjected to an alternating voltage.

FIGS. 3A-3C are schematic diagrams illustrating different vibration modes of the piezoelectric pump 21. The piezoelectric element 22 and the diaphragm 28 are affixed to each other to form a unimorph structure, which is displaced in the thickness direction by driving the piezoelectric element 22. Specifically, when the piezoelectric element 22 tries to expand from a resting state, such as that illustrated in FIG. 3A, the diaphragm 28 bulges toward the piezoelectric element 22 (i.e., toward the bottom side) as illustrated in FIG. 3B to increase the volume of the pump chamber 25. Thus, a negative pressure is generated in the pump chamber 25 and transmitted to the flow passage 24 communicating with the pump chamber 25, and a fluid in the flow passage 24 is suctioned into the pump chamber 25.

When the piezoelectric element 22 tries to contract, the diaphragm 28 bulges toward the pump chamber 25 (i.e., toward the top side) as illustrated in FIG. 3C to reduce the volume of the pump chamber 25. Since the pump chamber 25 and the discharge port 26 are disposed opposite each other with the flow passage 24 interposed therebetween, a fluid in the pump chamber 25 is discharged through the discharge port 26 to the outside. At the same time, a fluid in the flow passage 24 is drawn into the flow of the fluid from the pump chamber 25 and discharged through the discharge port 26.

As described above, in the piezoelectric pump 21, periodic changes in the volume of and pressure in the pump chamber 25 are repeatedly produced by bending and vibration of the piezoelectric element 22 and the diaphragm 28, and an inertial force begins to act on the flow of gas. This allows a fluid (gas) in the flow passage 24 to be constantly discharged from the discharge port 26. In the piezoelectric pump 21, the diaphragm 28 faces the discharge port 26 with the flow passage 24 and the pump chamber 25 interposed therebetween. This improves fluid efficiency of the piezoelectric pump 21, and allows even a high-viscosity fluid, such as nasal mucus, to be easily suctioned by the aspirator 10.

FIG. 4 is a block diagram of the circuit unit 31. The circuit unit 31 feeds back a current flowing through the piezoelectric element 22 to automatically regulate a drive voltage (output voltage) applied to the piezoelectric element 22. The circuit unit 31 includes a current detector 32, a regulator 33, a voltage controller 34, and a drive circuit 35. The current detector 32 measures a current flowing through the piezoelectric element 22. The regulator 33 determines the state of the front end of the nozzle 11 (hereinafter referred to as a nozzle end) on the basis of the measurement result of the current detector 32. The voltage controller 34 outputs a voltage having a predetermined pattern on the basis of the determination made by the regulator 33. The voltage controller 34 is supplied with power from a power source 36. The drive circuit 35 generates a drive voltage by boosting the voltage output by the voltage controller 34, and applies the drive voltage to the piezoelectric element 22. Note that the circuit unit 31 is obtained by mounting electronic components on a circuit board. The current detector 32 and the regulator 33 correspond to a detecting unit of the present disclosure. The regulator 33 and the voltage controller 34 correspond to a control unit of the present disclosure.

The nozzle end communicates with the suction port 27 of the piezoelectric pump 21 (see FIG. 2). This means that the current detector 32 and the regulator 33 detect the closed state of the suction port 27. Also, the regulator 33 and the voltage controller 34 regulate the output voltage for the piezoelectric element 22 in accordance with the detected closed state of the suction port 27. The indicator displays the detected closed state of the suction port 27.

Figure 5:
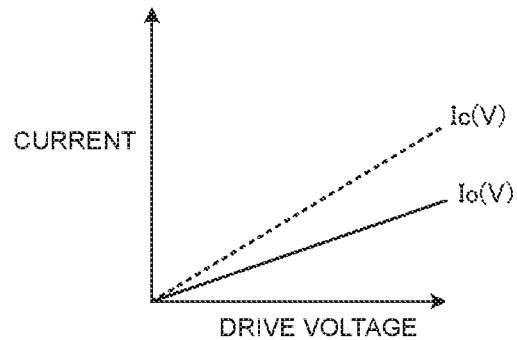
FIG. 5 is a graph showing the amplitude of current flowing through a piezoelectric element 22 with respect to the amplitude of drive voltage applied to the piezoelectric element 22.

FIG. 5 is a graph showing the amplitude of the current flowing through the piezoelectric element 22 with respect to the amplitude of the drive voltage applied to the piezoelectric element 22. For an amplitude V of each drive voltage, a current amplitude $I_c(V)$ obtained when the nozzle end is closed differs from a current amplitude $I_o(V)$ obtained when the nozzle end is open.

Thus, if a current amplitude I measured by the current detector 32 is close to the current amplitude $I_c(V)$, that is, if $|I-I_c(V)|<\delta$ holds for a predetermined value $\delta>0$, the regulator 33 determines that the nozzle end is closed. If the current amplitude I is close to the current amplitude $I_c(V)$, that is, if $|I-I_o(V)|<\delta$ holds, the regulator 33 determines that the nozzle end is open. The current amplitude $I_c(V)$ and the current amplitude $I_o(V)$ may be calculated as needed, or may be stored in the form of a table. Although the amplitude V of the drive voltage is held by the regulator 33, it may be acquired by measurement.

As illustrated in FIG. 5, for the amplitude V of each drive voltage, the current amplitude $I_c(V)$ is greater than the current amplitude $I_o(V)$. Therefore, the state of the nozzle end may be determined by comparing the current amplitude I with a threshold $I_t(V)$ which is appropriately set in the range of $I_o(V)<I_t(V)<I_c(V)$.

The magnitude of the impedance of the piezoelectric element 22 is the amplitude ratio between the current flowing through the piezoelectric element 22 and the drive voltage. This means that the determination made by the regulator 33 involves using the magnitude of the impedance of the piezoelectric element 22 at a drive frequency (i.e., the frequency of the drive voltage). Also, the suction pressure is high when the current amplitude I is close to the current amplitude $I_c(V)$ and low when the current amplitude I is close to the current amplitude $I_o(V)$. This means that the regulator 33 determines the state of the nozzle end by indirectly detecting the suction pressure. Here, the suction pressure is a pressure difference between the side of the suction port 27 and the side of the discharge port 26 in the piezoelectric pump 21 (see FIG. 2). Also, the flow rate is low when the current amplitude I is close to the current amplitude $I_c(V)$ and high when the current amplitude I is close to the current amplitude $I_o(V)$. This means that the regulator 33 determines the state of the nozzle end by indirectly detecting the flow rate. Here, the flow rate is the amount of air flowing from the suction port 27 to the discharge port 26 of the piezoelectric pump 21.

Figure 6:
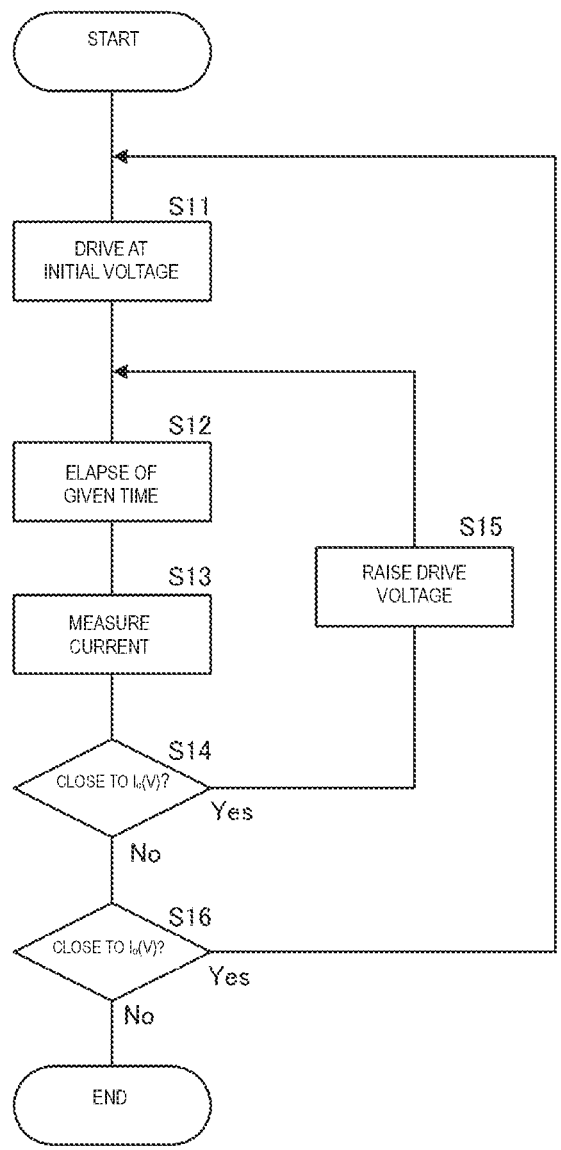
FIG. 6 is a flowchart illustrating an operation of the circuit unit according to the first embodiment.

FIG. 6 is a flowchart illustrating an operation of the circuit unit 31. The drive circuit 35 applies an initial voltage as a drive voltage to the piezoelectric element 22 (S11). After the elapse of a given time (e.g., about 1 second) (S12), the current detector 32 measures a current flowing through the piezoelectric element 22 (S13). If the current amplitude I of the measured current is close to the current amplitude $I_c(V)$, the regulator 33 determines that the nozzle end is closed, that is, the suctioning of nasal mucus has failed (Yes in S14). In this case, for removal of the nasal mucus, the drive circuit 35 applies a drive voltage having an amplitude greater by a predetermined value than the original amplitude to the piezoelectric element 22 (S15). If increasing the amplitude of the drive voltage causes it to exceed a limit value, the amplitude of the drive voltage is kept the same as the original amplitude.

If the current amplitude I is close to the current amplitude $I_o(V)$, the regulator 33 determines that the nozzle end is open (No in S14, Yes in S16). That is, the regulator 33 determines that suctioning of the nasal mucus has succeeded, or that the nozzle end is not in contact with the nasal mucus in the nasal cavity. In this case, step S11 is performed again. If the current amplitude I is far from both the current amplitude $I_c(V)$ and the current amplitude $I_o(V)$, the regulator 33 determines that the aspirator 10 has malfunctioned (No in S14, No in S16). In this case, the suctioning operation is terminated and the indicator displays an error message. If the current amplitude I is close to the current amplitude $I_o(V)$, the regulator 33 may terminate the suctioning operation on the basis of the determination that the suctioning of the nasal mucus has succeeded.

Figure 7A:
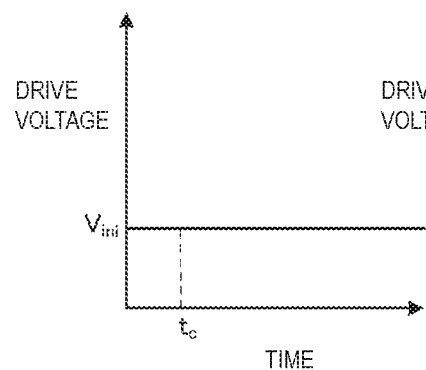
FIG. 7A is a conceptual diagram illustrating how the amplitude of drive voltage changes with time in suctioning of low-viscosity nasal mucus.
Figure 7B:
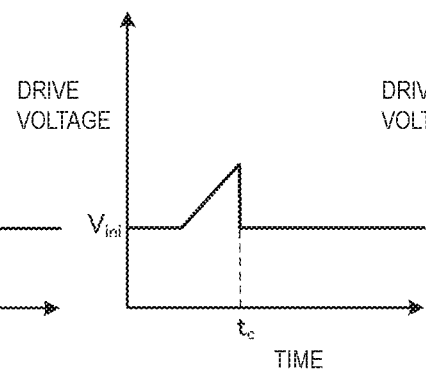
FIG. 7B is a conceptual diagram illustrating how the amplitude of drive voltage changes with time in suctioning of medium-viscosity nasal mucus.
Figure 7C:
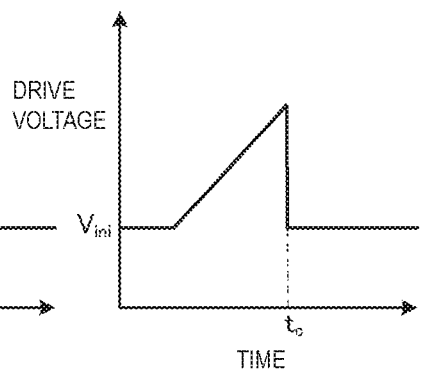
FIG. 7C is a conceptual diagram illustrating how the amplitude of drive voltage changes with time in suctioning of high-viscosity nasal mucus.

FIG. 7A is a conceptual diagram illustrating how the amplitude of the drive voltage changes with time in suctioning of low-viscosity nasal mucus. FIG. 7B is a conceptual diagram illustrating how the amplitude of the drive voltage changes with time in suctioning of medium-viscosity nasal mucus. FIG. 7C is a conceptual diagram illustrating how the amplitude of the drive voltage changes with time in suctioning of high-viscosity nasal mucus. Time $t_c$ represents the time when suctioning of nasal mucus has been completed. Note that the time difference between voltage adjustment and current measurement is not taken into account in FIGS. 7A-7C.

FIG. 7A shows that suctioning of low-viscosity nasal mucus is completed when the amplitude of the drive voltage is at an initial voltage amplitude $V_{ini}$; that is, the amplitude of the drive voltage is kept unchanged. FIG. 7B shows that in suctioning of medium-viscosity nasal mucus, the amplitude of the drive voltage increases with time from the initial voltage amplitude $V_{ini}$, and returns to the initial voltage amplitude $V_{ini}$ at the completion of the suctioning. FIG. 7C shows that in suctioning of high-viscosity nasal mucus, as compared to the case of suctioning the medium-viscosity nasal mucus, it takes more time to complete the suctioning and the amplitude of the drive voltage at the completion of the suctioning is larger. The aspirator 10 thus automatically regulates the drive voltage in accordance with the viscosity of the nasal mucus.

Figure 8A:
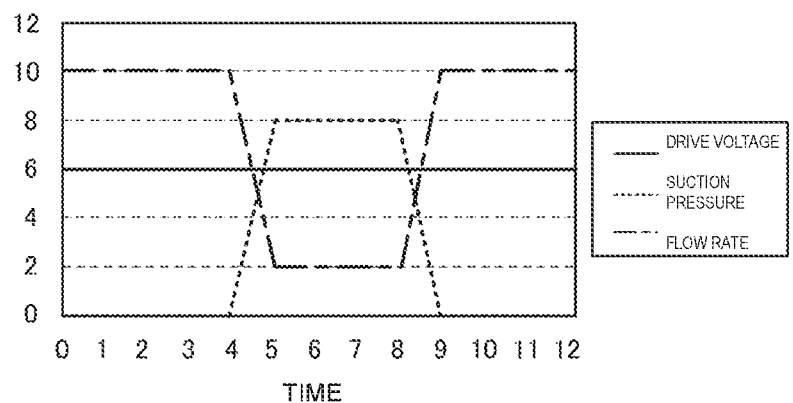
FIG. 8A is a conceptual diagram illustrating how the amplitude of drive voltage, the suction pressure, and the flow rate change with time in an aspirator having a conventional configuration.
Figure 8B:
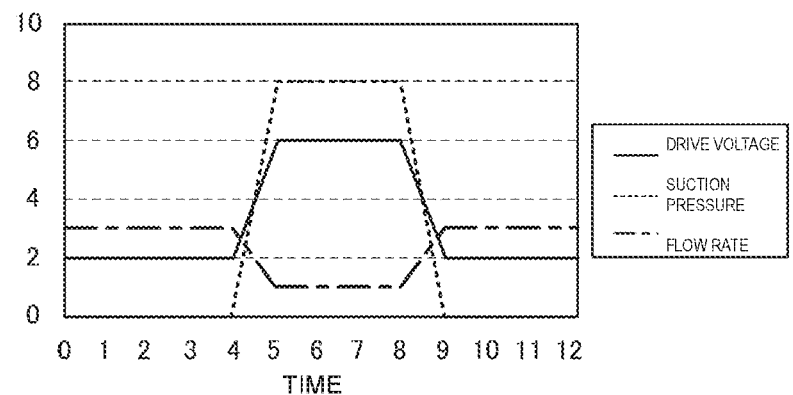
FIG. 8B is a conceptual diagram illustrating how the amplitude of drive voltage, the suction pressure, and the flow rate change with time in the aspirator according to the first embodiment.

FIG. 8A is a conceptual diagram illustrating how the amplitude of drive voltage, the suction pressure, and the flow rate change with time in an aspirator having a conventional configuration. FIG. 8B is a conceptual diagram illustrating how the amplitude of drive voltage, the suction pressure, and the flow rate change with time in the aspirator 10. Note that the amplitude of drive voltage, the suction pressure, the flow rate, and time are appropriately normalized in FIGS. 8A and 8B.

In the aspirator having the conventional configuration, as illustrated in FIG. 8A, the amplitude of the drive voltage is always constant. In the range of time from 0 to 4 and from 9 to 12, the suction pressure is 0 because the nozzle end is open, and the flow rate is excessively high because the amplitude of the drive voltage is regulated to be suitable for the nozzle end in the closed state. In the range of time from 4 to 9, where the nozzle end is closed, the suction pressure is higher than that when the nozzle end is open, and the flow rate is lower than that when the nozzle end is open.

In the aspirator 10, the amplitude of the drive voltage is automatically regulated as illustrated in FIG. 8B. In the range of time from 0 to 4 and from 9 to 12, the suction pressure is 0 because the nozzle end is open. Also, the amplitude of the drive voltage is kept small, and the flow rate is kept at a moderate level. In the range of time from 4 to 9, the nozzle end is closed. Accordingly, the amplitude of the drive voltage is greater than that when the nozzle end is open, and the suction pressure is higher than that when the nozzle end is open. Because of the large amplitude of the drive voltage, the flow rate is not significantly reduced from that when the nozzle end is open.

Every time the aspirator 10 determines that the nozzle end is closed, the aspirator 10 increases the amplitude of the drive voltage. Also, when the aspirator 10 determines that the nozzle end is open, the aspirator 10 reduces the amplitude of the drive voltage. Thus, when it is difficult to suction the nasal mucus, the amplitude of the drive voltage is increased and the nasal mucus is suctioned by high suction pressure. When it is easy to suction the nasal mucus, the amplitude of the drive voltage is kept at a medium level, and the nasal mucus is suctioned by low suction pressure. When suctioning of the nasal mucus is completed or there is no nasal mucus, the amplitude of the drive voltage is reduced. Thus, with the aspirator 10, the nasal mucus can be suctioned by appropriate suction pressure in accordance with the closed state of the nozzle end. Additionally, since the aspirator 10 can operate at a minimum drive voltage, power consumption during operation can be reduced. Also, when suctioning of the nasal mucus is completed or there is no nasal mucus, the amplitude of the drive voltage is reduced and it is unlikely that a large amount of air is suctioned out of the nasal cavity. A negative impact on the human body can thus be reduced.

Second Embodiment

Figure 9:
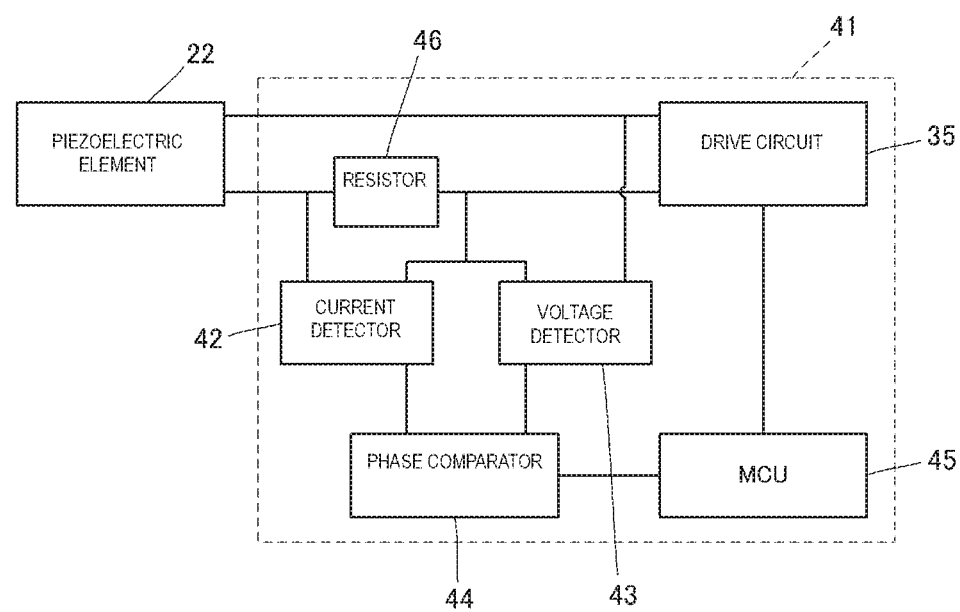
FIG. 9 is a block diagram of a circuit unit according to a second embodiment.

An aspirator according to a second embodiment of the present disclosure will be described. FIG. 9 is a block diagram of a circuit unit 41 according to the second embodiment. The circuit unit 41 includes a current detector 42, a voltage detector 43, a phase comparator 44, a microcontroller (MCU) 45, and a resistor 46. The current detector 42 measures a current flowing through the piezoelectric element 22 by measuring a voltage across both ends of the resistor 46 whose resistance value is known. The resistor 46 is inserted in a voltage line that connects the piezoelectric element 22 to the drive circuit 35. The voltage detector 43 measures a drive voltage applied to the piezoelectric element 22. The phase comparator 44 outputs a phase difference θ between the current measured by the current detector 42 and the voltage measured by the voltage detector 43. The microcontroller 45 outputs a voltage having a predetermined pattern to the drive circuit 35 on the basis of the phase difference θ output by the phase comparator 44.

A circuit-type digital comparator, such as a phase frequency comparator used in a phase-locked loop (PLL) or the like, is used as the phase comparator 44. The microcontroller 45 used is one having an I/O terminal and a PWM output terminal. The I/O terminal is connected to the phase comparator 44, and the PWM output terminal is connected to the drive circuit 35.

A phase difference $θ_c$ between the current flowing through the piezoelectric element 22 and the drive voltage when the nozzle end is closed differs from a phase difference $θ_o$ between the current flowing through the piezoelectric element 22 and the drive voltage when the nozzle end is open. Therefore, when the phase difference θ is close to the phase difference $θ_c$, the microcontroller 45 determines that the nozzle end is closed, whereas when the phase difference θ is close to the phase difference $θ_o$, the microcontroller 45 determines that the nozzle end is open. The phase of the impedance of the piezoelectric element 22 is a phase difference between the current flowing through the piezoelectric element 22 and the drive voltage. This means that the determination made by the microcontroller 45 involves using the phase of the impedance of the piezoelectric element 22 at a drive frequency.

Figure 10:
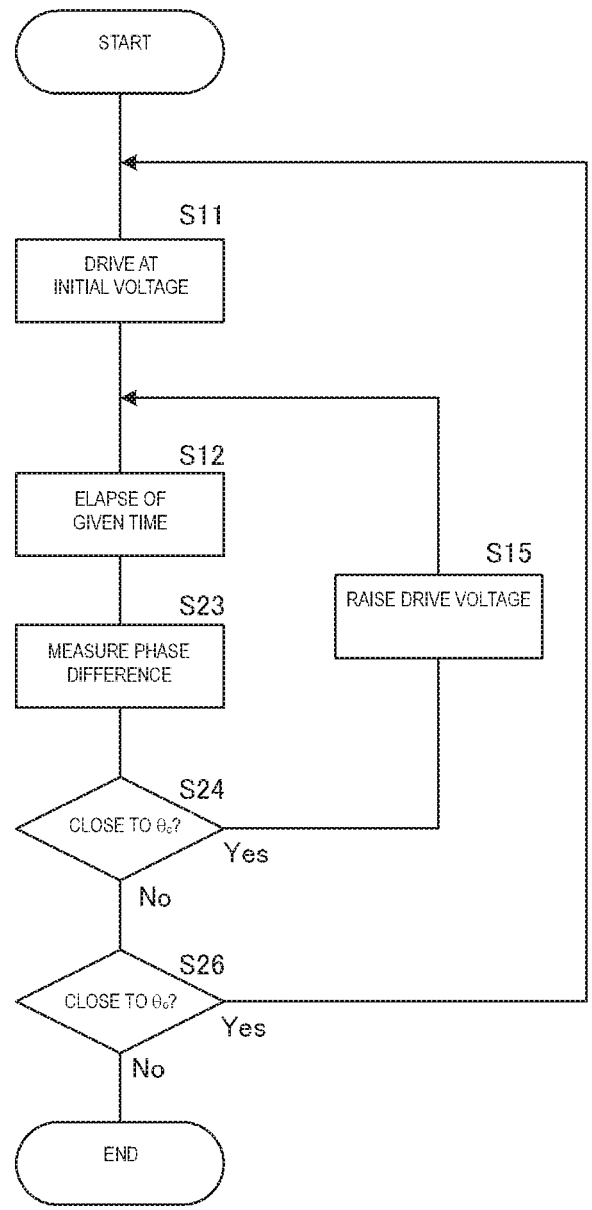
FIG. 10 is a flowchart illustrating an operation of the circuit unit according to the second embodiment.

FIG. 10 is a flowchart illustrating an operation of the circuit unit 41. The phase comparator 44 outputs a phase difference θ after step S12 (S23). The microcontroller 45 compares the phase difference θ with the phase difference $θ_c$, and also compares the phase difference θ with the phase difference $θ_o$ if necessary, thereby determining the state of the nozzle end (S24, S26).

In the second embodiment, the state of the nozzle end can be detected by measuring the phase difference θ between the current flowing through the piezoelectric element 22 and the drive voltage. Since the measurement of the phase difference θ is less affected by changes in temperature, it is possible to accurately regulate the suction pressure.

Third Embodiment

Figure 11:
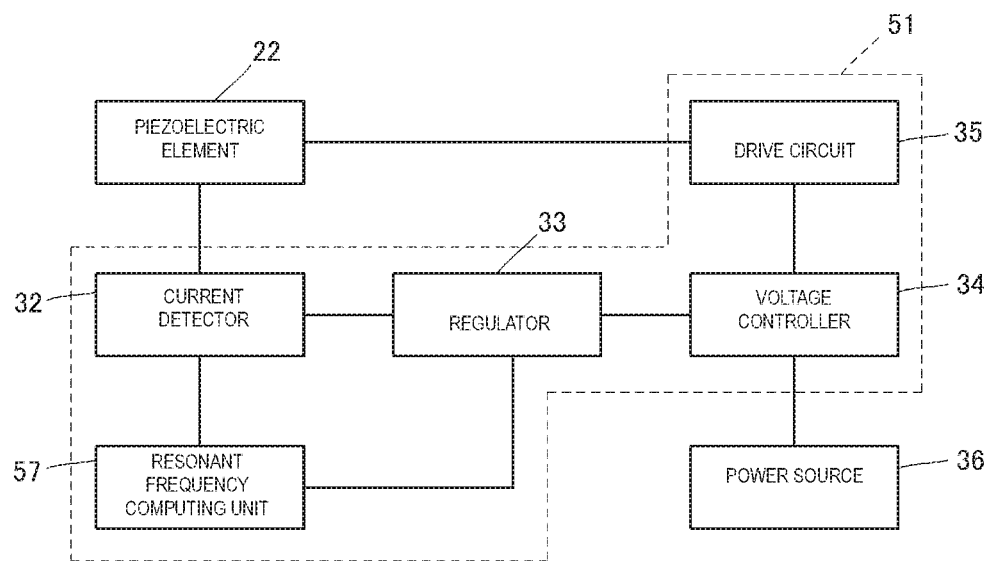
FIG. 11 is a block diagram of a circuit unit according to a third embodiment.

An aspirator according to a third embodiment of the present disclosure will be described. FIG. 11 is a block diagram of a circuit unit 51 according to the third embodiment. The circuit unit 51 includes a resonant frequency computing unit 57. The resonant frequency computing unit 57 calculates a resonant frequency f of the piezoelectric element 22 on the basis of the current measured by the current detector 32. The regulator 33 determines the state of the nozzle end on the basis of the resonant frequency f calculated by the resonant frequency computing unit 57.

The resonant frequency of the piezoelectric element 22 is a frequency at which the magnitude of the impedance of the piezoelectric element 22 is minimized, that is, a frequency at which the amplitude of the current flowing through the piezoelectric element 22 is maximized. The resonant frequency of the piezoelectric element 22 can be calculated by varying the drive frequency within a predetermined range, measuring the current flowing through the piezoelectric element 22 at each frequency, and selecting a frequency at which the amplitude of the measured current is maximized.

A resonant frequency $f_c$ of the piezoelectric element 22 when the nozzle end is closed differs from a resonant frequency $f_o$ of the piezoelectric element 22 when the nozzle end is open. Therefore, when the resonant frequency f is close to the resonant frequency $f_c$, the regulator 33 determines that the nozzle end is closed, whereas when the resonant frequency f is close to the resonant frequency $f_o$, the regulator 33 determines that the nozzle end is open.

Figure 12:
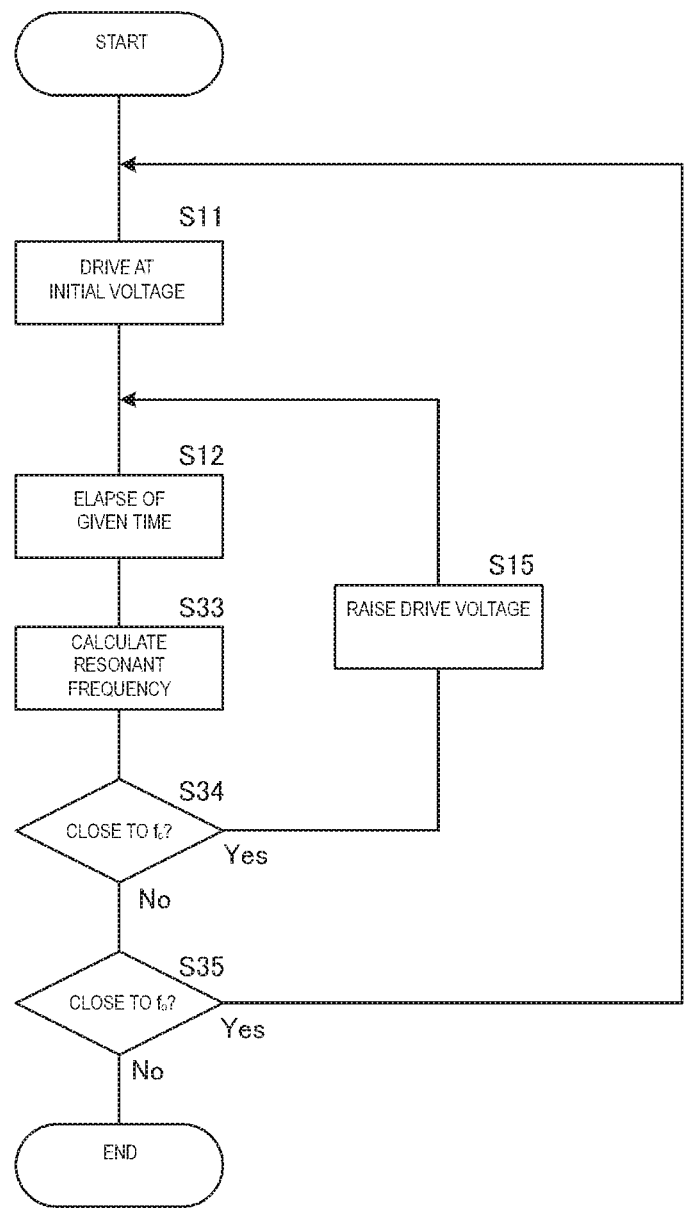
FIG. 12 is a flowchart illustrating an operation of the circuit unit according to the third embodiment.

FIG. 12 is a flowchart illustrating an operation of the circuit unit 51. The resonant frequency computing unit 57 calculates the resonant frequency f after step S12 (S33). The regulator 33 compares the resonant frequency f with the resonant frequency $f_c$, and also compares the resonant frequency f with the resonant frequency $f_o$ if necessary, thereby determining the state of the nozzle end (S34, S36). The drive circuit 35 applies a drive voltage appropriate for the state of the nozzle end to the piezoelectric element 22 (S11, S15). The drive frequency is adjusted to the resonant frequency f.

In the third embodiment, the state of the nozzle end can be detected by calculating the resonant frequency f of the piezoelectric element 22. Also, by adjusting the drive frequency to the resonant frequency f, it is possible to increase the vibration of the piezoelectric element 22 and achieve high suction pressure without necessarily varying the amplitude of the drive voltage.

Although the aspirator of each of the embodiments described above is a nasal mucus aspirator, the aspirator of the present disclosure is not limited to the nasal mucus aspirator, and may be one that suctions body fluid, such as saliva or phlegm.

Fourth Embodiment

Figure 13:
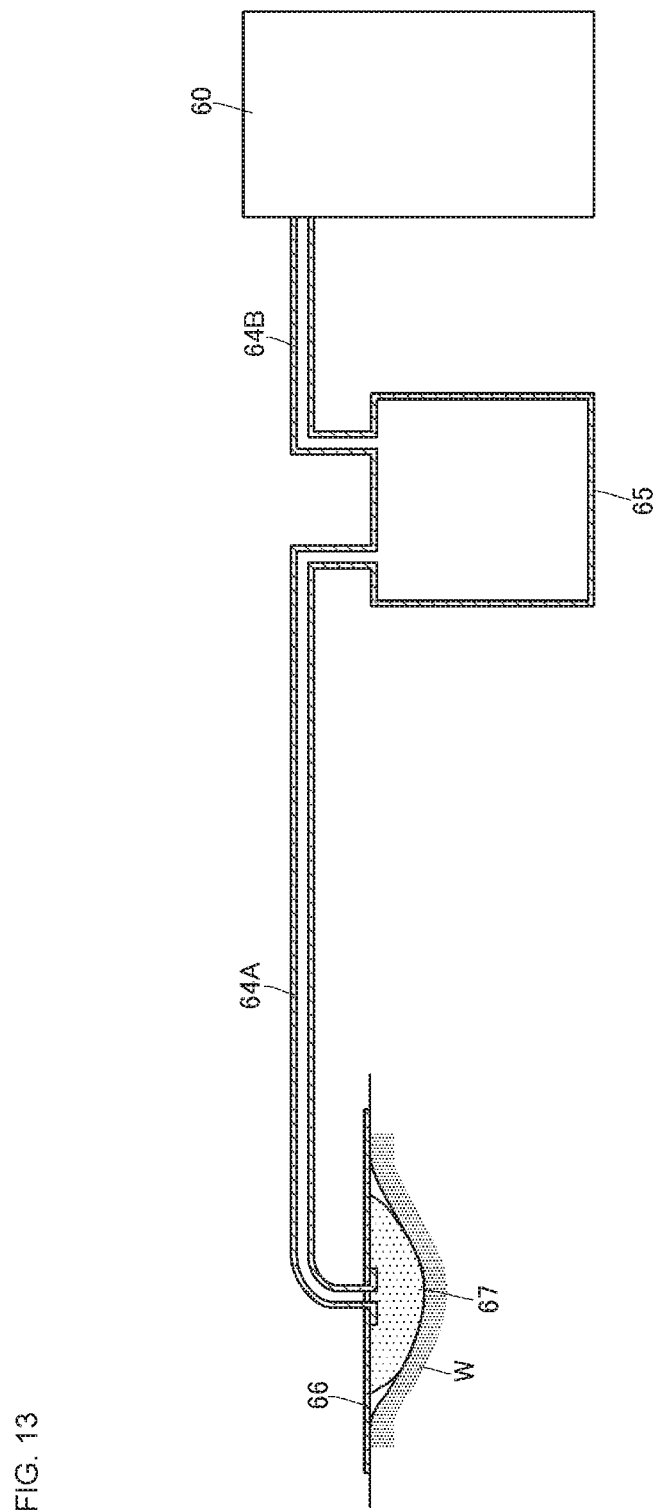
FIG. 13 is a schematic cross-sectional view for explaining a negative pressure wound therapy according to a fourth embodiment.

An aspirator for a negative pressure wound therapy according to a fourth embodiment of the present disclosure will be described. FIG. 13 is a schematic cross-sectional view for explaining a negative pressure wound therapy according to the fourth embodiment. The negative pressure wound therapy involves covering a wounded portion W of the patient with a dressing 67, such as a gauze dressing. The wounded portion W covered with the dressing 67 is hermetically sealed with a film 66. A first end of a tube 64A passes through an opening of the film 66 and is connected to the dressing 67. A second end of the tube 64A is connected to a storage unit 65. The storage unit 65 is connected to an aspirator 60 by a tube 64B extending therebetween. A flow passage that connects the dressing 67 to the aspirator 60 is thus created.

The aspirator 60 has, for example, the same configuration as the piezoelectric drive unit of the first embodiment. The piezoelectric drive unit includes a piezoelectric pump and a circuit unit for driving the piezoelectric pump, as described above. In the negative pressure wound therapy, the aspirator 60 suctions air in the dressing 67 to lower the pressure in the dressing 67. Also, the negative pressure wound therapy involves suctioning exudate accumulated in the dressing 67 together with air, separating the exudate from the air, and storing the exudate in the storage unit 65.

Figure 14:
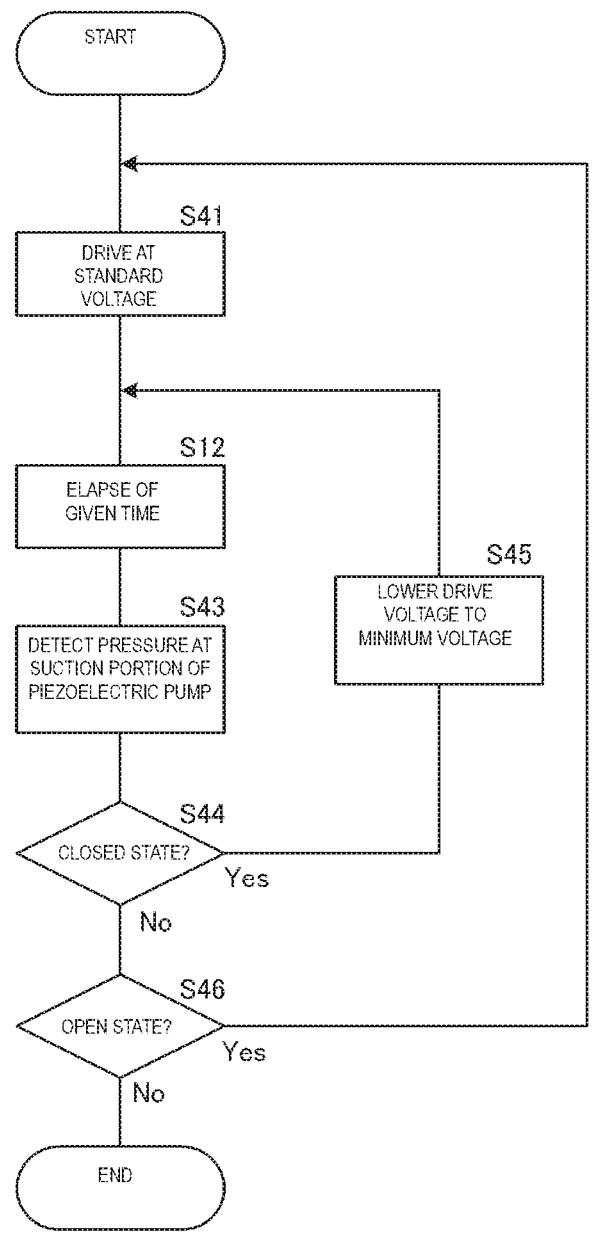
FIG. 14 is a flowchart illustrating an operation of an aspirator according to the fourth embodiment.

FIG. 14 is a flowchart illustrating an operation of the aspirator 60. The aspirator 60 operates in the following manner. The aspirator 60 sets the drive voltage of the piezoelectric pump to a standard voltage, and drives the piezoelectric pump to suction air in the dressing 67 (S41). When the pressure in the dressing 67 is lowered to a lower limit by this suctioning, a suction portion (suction port) of the piezoelectric pump approaches a closed state. After the elapse of a given time (S12), the aspirator 60 detects the state of the suction portion of the piezoelectric pump (S43). For example, as in the first embodiment described above, the state of the suction portion of the piezoelectric pump is detected by measuring current flowing through a piezoelectric element of the piezoelectric pump. If the suction portion of the piezoelectric pump is detected to be in the closed state (Yes in S44), the aspirator 60 lowers the drive voltage of the piezoelectric pump to a minimum voltage at which detection of the closed state is generally possible (S45). Then, the aspirator 60 performs step S12 again.

Lowering the drive voltage of the piezoelectric pump lowers the suction force of the piezoelectric pump. As time elapses, air begins to flow into the dressing 67 through a narrow gap between the film 66 and the skin of the patient, or between the film 66 and the tube 64A. When this causes the pressure in the dressing 67 to reach an upper limit, the suction portion of the piezoelectric pump approaches the open state. If suctioning of air in the dressing 67 is not yet sufficient enough, the suction portion of the piezoelectric pump remains close to the open state. If the suction portion of the piezoelectric pump is detected to be in the open state (No in S44, Yes in S46), the aspirator 60 drives the piezoelectric pump at the standard voltage to suction air in the dressing 67 (S41). If the suction portion of the piezoelectric pump is detected to be neither in the closed state nor in the open state (No in S44, No in S46), the aspirator 60 determines that a malfunction has occurred, and terminates the suctioning operation.

In the fourth embodiment, when pressure in the dressing 67 reaches a lower limit, the drive voltage of the piezoelectric pump is lowered to a minimum voltage. This makes it possible not only to prevent excessive suction, but also to reduce power consumption. Also, when pressure in the dressing 67 reaches an upper limit, suctioning of air in the dressing 67 is resumed. It is thus possible to keep pressure in the dressing 67 at a low level.

Fifth Embodiment

Figure 15A:
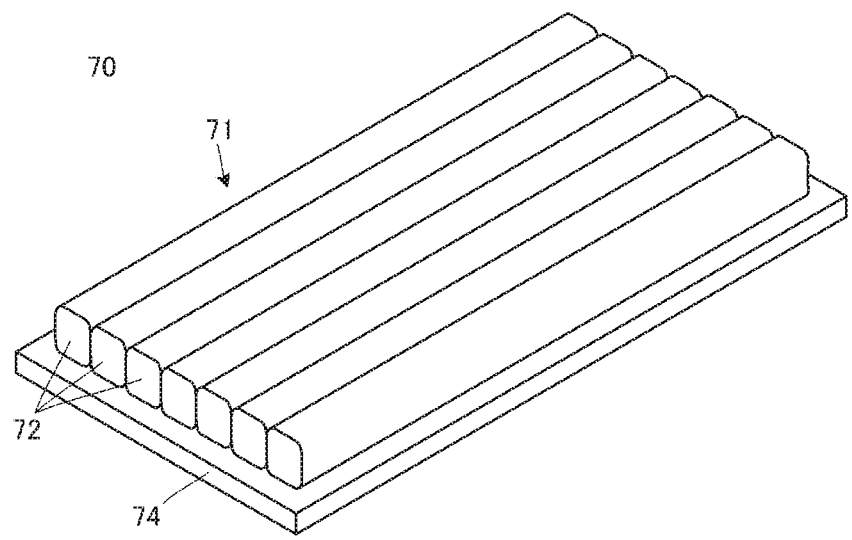
FIGS. 15A and 15B provide external perspective views and an exploded perspective view of an anti-bedsore bed according to a fifth embodiment.
Figure 15B:
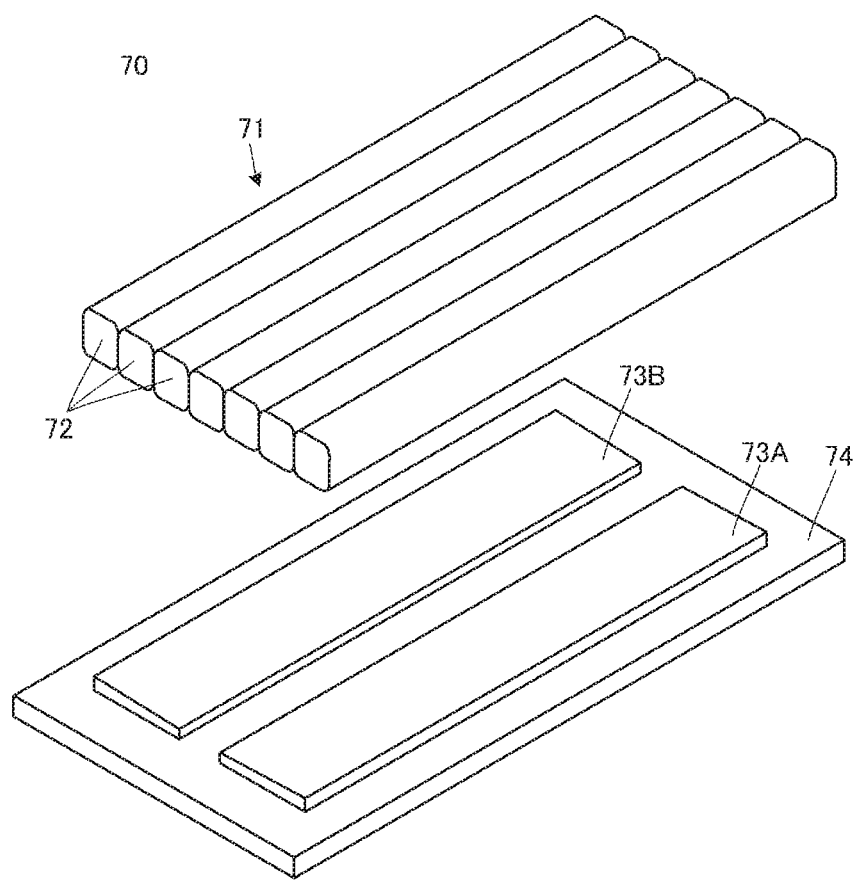

An anti-bedsore bed using a pressurizer according to a fifth embodiment of the present disclosure will be described. FIG. 15A is an external perspective view of an anti-bedsore bed 70 according to the fifth embodiment. FIG. 15B is an exploded perspective view of the anti-bedsore bed 70 according to the fifth embodiment. A rectangular upper surface of a base 74 is provided with air cells 73A and 73B thereon. The air cells 73A and 73B are arranged side by side in the direction of the short side of the upper surface of the base 74, and are longer in the longitudinal direction of the upper surface of the base 74. A mat 71 formed by joining the side faces of a plurality of columnar air cells 72 is placed over the upper surface of the base 74 having the air cells 73A and 73B thereon.

The air cells 72, 73A, and 73B are connected by corresponding tubes (not shown) to a pressurizer (not shown). The pressurizer includes piezoelectric pumps corresponding to the respective air cells, drive circuit units for driving the respective piezoelectric pumps, and a control circuit unit configured to control the timing of the operation of each of the drive circuit units. The piezoelectric pumps are each configured, for example, in the same manner as in the first embodiment. The drive circuit units are each configured, for example, in the same manner as the circuit unit of the first embodiment. The piezoelectric pumps are each positioned with its discharge portion (discharge port) facing the corresponding tube and its suction portion facing the outside air.

The tube connected to the air cells 72 is provided with a valve. This allows air to be introduced into or discharged from the air cells 72 as necessary. The tubes connected to the air cells 73A and 73B are not provided with any valves. Thus, when the piezoelectric pumps are driven, air is supplied to the air cells 73A and 73B, which are thus pressurized. When the piezoelectric pumps are stopped, air is discharged from the air cells 73A and 73B, and the pressure in the air cells 73A and 73B is reduced.

Figure 16A:
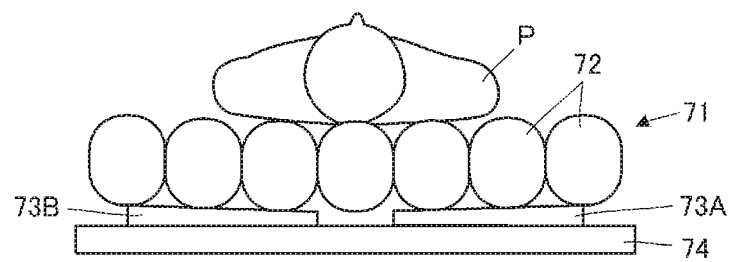
FIGS. 16A and 16B provide side views of the anti-bedsore bed according to the fifth embodiment.
Figure 16B:
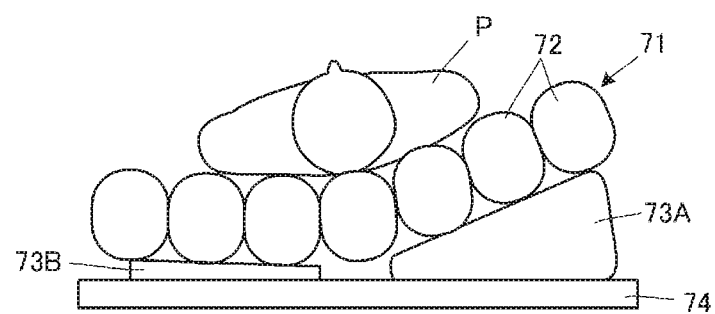

FIG. 16A is a side view of the anti-bedsore bed 70. FIG. 16B is a side view of the anti-bedsore bed 70 in which the air cell 73A is inflated. In the anti-bedsore bed 70, one of the air cells 73A and 73B is inflated by the pressurizer to raise one side of the body of a user P. This allows the user P to turn over. The air cells 72 may be used, along with the air cells 73A and 73B, to allow the user P to turn over.

Figure 17:
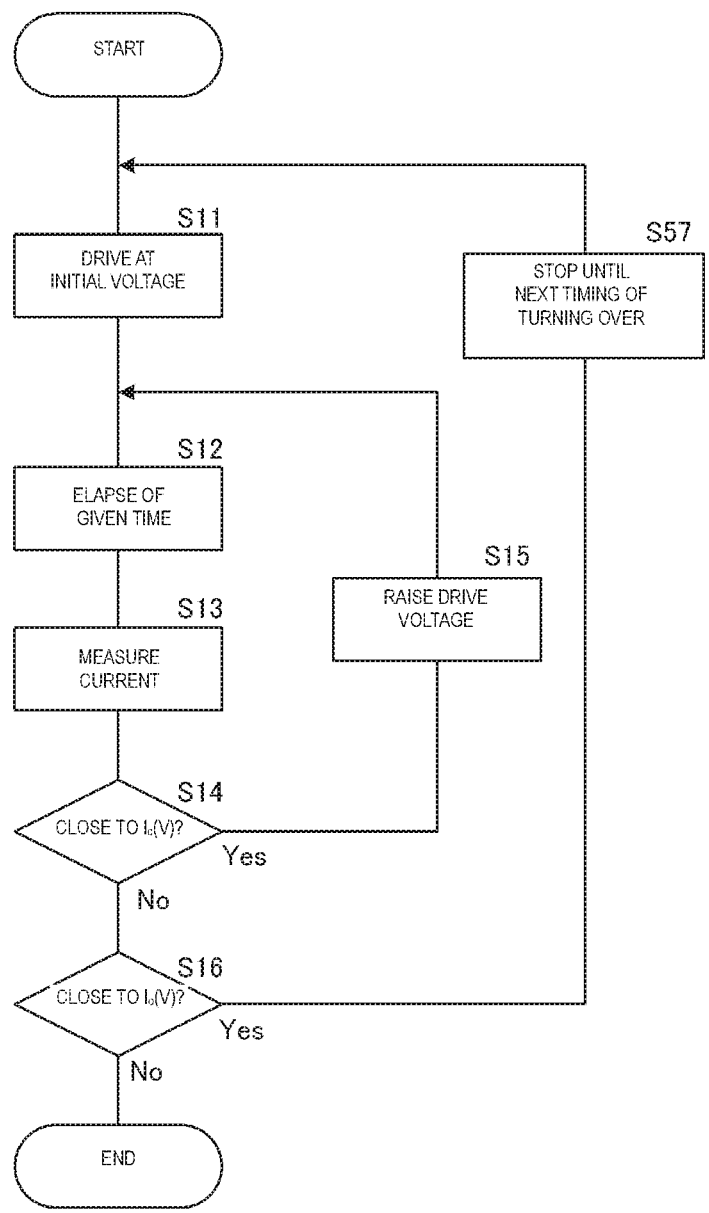
FIG. 17 is a flowchart illustrating an operation of a drive circuit unit corresponding to an air cell 73A.

FIG. 17 is a flowchart illustrating an operation of the drive circuit unit corresponding to the air cell 73A. The drive circuit unit corresponding to the air cell 73B operates in the same manner as the drive circuit unit corresponding to the air cell 73A. The drive circuit unit operates in the following manner. After driving the piezoelectric pump corresponding to the air cell 73A at an initial voltage (S11) and a given time (e.g., about 0.1 seconds) elapses (S12), the drive circuit unit measures a current flowing through the piezoelectric pump corresponding to the air cell 73A (S13). If the user has not yet turned over, the air cell 73A is held under pressure by the weight of the user. Therefore, the current flowing through the piezoelectric pump corresponding to the air cell 73A is close to the current amplitude $I_c(V)$ obtained when the discharge portion of the piezoelectric pump is in the closed state. Accordingly, if the amplitude of the measured current is close to the current amplitude $I_c(V)$, the drive circuit unit determines that the user has not turned over (Yes in S14). Then, the drive circuit unit raises the drive voltage of the piezoelectric pump corresponding to the air cell 73A to continue to apply pressure to the air cell 73A (S15).

When the user turns over, the body of the user is separated from the air cell 73A. This brings pressure in the air cell 73A close to the atmospheric pressure. Therefore, the current flowing through the piezoelectric pump corresponding to the air cell 73A is close to the current amplitude $I_o(V)$ obtained when the discharge portion of the piezoelectric pump is open. Accordingly, if the amplitude of the measured current is close to the current amplitude $I_o(V)$ (No in S14, Yes in S16), the drive circuit unit determines that the user has turned over. Then, the drive circuit unit stops the piezoelectric pump corresponding to the air cell 73A to stop the application of pressure to the air cell 73A until the next timing of turning over (S57). At the next timing of turning over, the drive circuit unit drives the piezoelectric pump corresponding to the air cell 73A at the initial voltage again (S11). Note that the timing of operation of each of the drive circuit units corresponding to the air cells 73A and 73B is controlled by the control circuit unit such that the air cells 73A and 73B are alternately pressurized.

In the fifth embodiment, the amplitude of the drive voltage of the piezoelectric pump is increased when the user does not turn over, whereas the piezoelectric pump is stopped when the user turns over. Thus, by simply driving the piezoelectric pump for a minimum period of time at a minimum output, it is possible to allow the user to turn over and prevent the user's bedsore. In step S15 of the fifth embodiment, the drive circuit unit may keep the drive voltage of the piezoelectric pump unchanged, instead of raising it. Even in this case, an effect close to that in the case of raising the drive voltage of the piezoelectric pump can be achieved.

REFERENCE SIGNS LIST 10, 60: aspirator
11: nozzle
12: separator
13: piezoelectric drive unit
14, 24: flow passage
15, 65: storage unit
21: piezoelectric pump (pump)
22: piezoelectric element
23: structure
25: pump chamber
26: discharge port (discharge portion)
27: suction port (suction portion)
28: diaphragm
31, 41, 51: circuit unit
32, 42: current detector (detecting unit)
33: regulator (detecting unit, control unit)
34: voltage controller (control unit)
35: drive circuit
36: power source
43: voltage detector
44: phase comparator
45: microcontroller
46: resistor
57: resonant frequency computing unit
64A, 64B: tube
66: film
67: dressing
70: anti-bedsore bed
71: mat
72, 73A, 73B: air cell
74: base
P: user
W: wounded portion

The invention claimed is:

1. An aspirator or pressurizer comprising:
a pump driven by a piezoelectric element and having an inlet and an outlet; and
a circuit configured to:
  detect whether the inlet or the outlet is in a closed state; and
  regulate a voltage output to the piezoelectric element based on detection of the closed state of the inlet or the outlet,
wherein the circuit is further configured to detect the closed state in part by detecting an impedance of the piezoelectric element, and wherein the circuit detects that the inlet or the outlet is in the closed state when a measured amplitude of current flowing through the piezoelectric element is greater than a threshold amplitude.

2. The aspirator or pressurizer according to claim 1, wherein the circuit is configured to lower the voltage output to the piezoelectric element if the circuit detects that the inlet or the outlet is in the closed state.

3. The aspirator or pressurizer according to claim 1, wherein the circuit is configured to raise the voltage output to the piezoelectric element if the circuit detects that the inlet or the outlet is in the closed state.

4. The aspirator or pressurizer according to claim 1, further comprising an indicator configured to display an indication of the closed state of the inlet or the outlet.

5. The aspirator or pressurizer according to claim 1, wherein an object to be suctioned by the aspirator or pressurizer is nasal mucus.

6. An aspirator or pressurizer comprising:
a pump driven by a piezoelectric element and having an inlet and an outlet; and
a circuit configured to:
  detect whether the inlet or the outlet is in a closed state; and
  regulate a voltage output to the piezoelectric element based on detection of the closed state of the inlet or the outlet,
wherein the circuit is further configured to detect the closed state in part by detecting an impedance of the piezoelectric element, wherein the circuit is configured to detect the closed state in part by using a frequency at which a magnitude of the impedance of the piezoelectric element is minimized.

7. An aspirator or pressurizer comprising:
a pump having an inlet and an outlet; and
a circuit configured to:
  detect whether the inlet or the outlet is in a closed state or an open state;
  raise a drive voltage of the pump when the circuit detects that the inlet or the outlet is in the closed state; and
  lower the drive voltage of the pump when the circuit detects that the inlet or the outlet is in the open state,
wherein the circuit detects that the inlet or the outlet is in the closed state when a measured amplitude of current flowing through a piezoelectric element is greater than a threshold amplitude.

8. The aspirator or pressurizer according to claim 7, wherein the piezoelectric element is driven by the drive voltage.

9. The aspirator or pressurizer according to claim 7, wherein the circuit is further configured to detect whether a flow passage communicating with the suction portion or the discharge portion is in a closed state.

* * * * *

UNITED STATES PATENT AND TRADEMARK OFFICE
CERTIFICATE OF CORRECTION

PATENT NO. : 11,052,006 B2
APPLICATION NO. : 15/401552
DATED : July 6, 2021
INVENTOR(S) : Nobuhira Tanaka et al.

It is certified that error appears in the above-identified patent and that said Letters Patent is hereby corrected as shown below:

In the Specification

Column 6, Line 51, "I-$I_c$(V)|" should be -- |I-$I_c$(V)| --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*